United States Patent [19]

Jochum et al.

[11] Patent Number: 5,147,904
[45] Date of Patent: Sep. 15, 1992

[54] OPEN-PORED MOLDINGS, A PROCESS FOR THEIR PRODUCTION AND USE THEREOF

[75] Inventors: Peter Jochum; Oswald Gasser, both of Seefeld; Manfred Holupirek, Grafrath; Erich Wanek, Seefeld; Rainer Guggenberger, Hersching; Klaus-Peter Stefan, Seefeld; Klaus Ellrich, Wörthsee, all of Fed. Rep. of Germany

[73] Assignee: Thera Patent GmbH & Co. KG, Seefeld, Fed. Rep. of Germany

[21] Appl. No.: 570,808

[22] Filed: Aug. 22, 1990

[30] Foreign Application Priority Data

Aug. 24, 1989 [DE] Fed. Rep. of Germany ....... 3927984

[51] Int. Cl.⁵ .................................. A61F 2/28
[52] U.S. Cl. .................................. 523/115; 523/116; 524/5; 521/79; 521/91; 521/92; 521/97
[58] Field of Search .................... 523/116, 115; 524/5; 521/79, 97, 91, 92

[56] References Cited

U.S. PATENT DOCUMENTS

| | | | |
|---|---|---|---|
| 4,190,710 | 2/1980 | Ley et al. | 521/89 |
| 4,209,434 | 6/1980 | Wilson et al. | 524/443 |
| 4,296,209 | 10/1981 | Tomic | 521/85 |
| 4,360,605 | 11/1982 | Schmitt et al. | 523/116 |
| 4,376,835 | 3/1983 | Schmitt et al. | 523/116 |
| 4,569,954 | 2/1986 | Wilson et al. | 523/116 |
| 4,602,048 | 7/1986 | Penton et al. | 521/82 |
| 4,842,603 | 6/1989 | Draenert | 623/16 |
| 4,870,113 | 9/1989 | Mueller et al. | 521/89 |
| 4,927,866 | 5/1990 | Purrmann et al. | 523/115 |
| 4,940,730 | 7/1990 | Kuphal et al. | 521/79 |

FOREIGN PATENT DOCUMENTS

| | | |
|---|---|---|
| 0023013 | 7/1980 | European Pat. Off. |
| 0024056 | 8/1980 | European Pat. Off. |
| 0241277 | 10/1987 | European Pat. Off. |
| 2061513 | 6/1971 | Fed. Rep. of Germany |
| 2319715 | 10/1973 | Fed. Rep. of Germany |
| 2736447 | 2/1978 | Fed. Rep. of Germany |
| 2752297 | 5/1979 | Fed. Rep. of Germany |
| 2929121 | 2/1981 | Fed. Rep. of Germany |
| 3325111 | 1/1985 | Fed. Rep. of Germany |
| 3806448 | 9/1989 | Fed. Rep. of Germany |
| 1316129 | 5/1973 | United Kingdom |
| 1548419 | 7/1979 | United Kingdom |

OTHER PUBLICATIONS

Ullmanns, Encyklopadie der technischen Chemie 4th Edition, 1982 Zahnarztliche Mitteilungen 77, 840 (1987), J. F. Osborne.

*Primary Examiner*—John Kight, III
*Assistant Examiner*—John M. Cooney, Jr.
*Attorney, Agent, or Firm*—Birch, Stewart, Kolasch & Birch

[57] ABSTRACT

Open-pored moldings containing the product of the foaming and setting of (a) an aluminum fluorosilicate glass, (b) at least one polycarboxylic acid with an average molecular weight of >500, (c) a foaming agent, other than carbonates and/or hydrogen-carbonates, (d) optionally a chelating agent and (e) water, are suitable in particular as bone substitute material.

Production is carried out by homogeneously mixing (a), (b), (c), optionally (d), and (e), then foaming, shaping and setting.

11 Claims, No Drawings

OPEN-PORED MOLDINGS, A PROCESS FOR THEIR PRODUCTION AND USE THEREOF

FIELD OF THE INVENTION

The present invention relates to open-pored moldings, a process for their production and use thereof.

BACKGROUND OF THE INVENTION

In surgical operations, the attending physician is often faced with the problem of having to repair natural bone defects or bone defects occurring during the operation. The primarily utilized bone substitute materials are bio-inert or bioactive materials and are known by the terms "bio-ceramics, bio-glasses and bio-glass ceramics". Hitherto, "bio-inert" has been understood to refer to materials which do not trigger tissue reactions and do not give off any foreign substances. One can also include in this category titanium implant bodies, which have a layer of titanium oxide on the surface, which in this case performs the task of the bio-inert ceramic layer. In current usage, "bioactive" is used to denote materials which have the property of uniting directly with osseous tissue. These include bio-glasses and bio-glass ceramics which have on the surface considerable proportions of calcium phosphate ceramics, such as hydroxyl apatite ceramics and tricalcium phosphate ceramics. Consequently, as bone substitute material, various hydroxyl apatite ceramics and tricalcium phosphate ceramics are used, which are available in granulated form as well as in pre-fabricated moldings. The production of the materials requires very expensive sintering processes during which micro- and macroporosity can be achieved by temperature and certain additives.

To counter bone defects, it is also known to use implant materials based on polyacrylates (e.g., PMMA), which are filled with filler particles based on tricalcium phosphate (German Offenlegungsschrift 33 25 111). The Offenlegungsschrift also discloses that it can be advantageous to add further physiologically compatible resorbable materials in addition to the tricalcium phosphate. A porosity is produced on the surface of the substitute material due to the resorption and this is intended to facilitate the establishment of osseous material.

In a similar manner, German Offenlegungsschrift 27 52 297 discloses filled polymethyl methacrylate materials, which in addition to a resorbable filler (e.g. $Na_2HPO_4$) contain carbonates and phosphoric acid. The interaction of phosphoric acid and carbonate produces a porous material structure upon admixing via a foaming process. Since, however, the materials contain liquid monomers and phosphoric acid, they are not toxicologically acceptable. In addition, high temperatures are to be anticipated during the setting reaction, during which adjoining tissue can be destroyed. In view of this, a "bioactive" effect is hardly possible.

For a considerable length of time, so-called "glass-ionomer cements" have been used in the field of dental medicine. These are reaction products of an aluminum fluorosilicate glass powder with a water-soluble polycarboxylic acid and water. These materials are used primarily for tooth-filling material and tooth-cement material; their use as bone cement, i.e., for fixing prostheses in bones, has also been described (see e.g. German Offenlegungsschrift 29 29 121).

German Offenlegungsschrift 27 36 447 discloses a process for the production of polymer ceramic materials from an ion-leachable glass powder and a polycarboxylic acid, in which the reaction components are not homogeneously mixed but sprayed on to a substrate surface in such a manner that the components are reacted with each other only after leaving the spray head. A blowing agent can be added to the two reaction components to provide foaming. The foaming that can be achieved with this spray process is not satisfactory for the present purposes, because the achievable total pore volume ($V_p$) is too low. For the purposes of the invention it is necessary to provide for open-pored moldings which have interconnected pores and a total pore volume ($V_p$) of at least 30% by volume, so that when the moldings are used as bone substitute material, the osseous material can grow right through the molded body without any difficulties and to an adequate extent. The materials disclosed in the Offenlegungsschrift are used primarily as building materials, e.g., as insulating construction bricks (see top of page 6).

German Offenlegungsschrift P 38 06 448 discloses porous moldings made from a workable material which contains no toxicologically unacceptable low-molecular monomers and which is bioactive. The porous moldings contain the product of the foaming and setting of (a) aluminum fluorosilicate glass, (b) at least one polycarboxylic acid with an average molecular weight of >500, (c) a carbonate and/or hydrogencarbonate as foaming agent, (d) optionally a chelating agent and (e) water, and are suitable as bone substitute material.

The present invention relates to a further development of these moldings.

SUMMARY OF THE INVENTION

One object of the present invention relates to open-pored moldings containing the product of the foaming and setting of (a) an aluminum fluorosilicate glass, (b) at least one polycarboxylic acid with an average molecular weight of >500, (c) a foaming agent, other than carbonates and/or hydrogencarbonates, (d) optionally a chelating agent and (e) water, the total pore volume ($V_p$) of the moldings being 30 to 70% by volume.

The open-pored moldings according to the invention are particularly suitable as bone substitute material. The pores are interconnected.

The open-pored moldings according to the invention preferably take the form of granules, parallelepipeds or anatomically shaped bodies as bone substitute material.

The total pore volume ($V_p$) of the open-pored moldings according to the invention is preferably 40 to 60% by volume.

A further object of the invention relates to the use of open-pored moldings, containing the product of the foaming and setting of (a) an aluminum fluorosilicate glass,
(b) at least one polycarboxylic acid with an average molecular weight of >500,
(c) a foaming agent, other than a carbonate and/or hydrogencarbonate,
(d) optionally a chelating agent, and
(e) water, for the production of implantable materials, and also the use of open-pored moldings, obtained by the foaming and setting of (a) an aluminum fluorosilicate glass,
(b) at least one polycarboxylic acid with an average molecular weight of >500, (c) a foaming agent, other than carbonates and/or hydrogencarbonates,
(d) optionally a chelating agent and
(e) water, for the production of granules, parallelepipeds or anatomically shaped bodies as bone-like implants.

The open-pored moldings according to the present invention can be produced by homogeneously intermixing (not spraying)
(a) an aluminum fluorosilicate glass,
(b) at least one polycarboxylic acid with an average molecular weight of >500,
(c) a foaming agent, other than carbonates and/or hydrogen carbonates,
(d) optionally a chelating agent, and
(e) water and foaming and setting the mixture with simultaneous and/or subsequent shaping.

DETAILED DESCRIPTION OF THE INVENTION

All materials which are able to effect foaming during the production of the moldings are suitable as foaming agents (c). By means of the liquid components ($H_2O$ or $H_2O$+acid), with added surfactants and/or emulsifiers and stirring in gases (e.g., air), it is, for example, possible to prepare stable foams to which the other components (e.g., glass) are then added (see, for example, Ullmanns Enzyklopaedie der technischen Chemie, Volume 22, p. 463, Verlag Chemie, 4th Edition, 1982). Metallic hydrides, particularly sodium hydroboride, which causes a foaming of the setting cement with protons (water or acids) with the evolution of hydrogen, are also suitable.

Another possibility for foam formation is the use of an aqueous solution of a gas, e.g., of $CO_2$ or $SO_2$, which is expelled by the added acid during the production of the cement and consequently brings about foaming.

It is also possible to add peroxides, e.g., $H_2O_2$, which result in foaming either by the action of acids or by metal catalysis with decomposition and the discharge of oxygen. It is, for example, possible to use an aqueous $H_2O_2$ solution for admixing the cement and to add to the powder a corresponding quantity of $FeSO_4$, which then, when the two components are brought together, brings about oxygen evolution and therefore foaming.

Further foaming agents are expanding agents, such as solid organic expanding agents, e.g., azodicarbonamide, azobis-(isobutyronitrile), diphenyloxide-disulphonic acid hydrazide or N-nitroso compounds, solid inorganic expanding agents, liquid expanding agents, e.g., hydrocarbons or halogenated hydrocarbons, and gaseous expanding agents, such as $N_2$, $CO_2$ and air.

Solid and liquid foaming agents are generally used in a concentration of 0.01–50% by weight, based on the total mixture, particularly preferred 0.1–20% by weight, while gaseous foaming agents are used in quantities of 5–90% by volume, based on the total mixture, preferably 10–60% by volume.

The foaming agent can foam up one to three of components (a), (b), (d) and (e) first, the remaining components being added subsequently. Pre-mixes of the components can, however, also be made, one of which contains the foaming agent, the components foaming only when added together. If the foaming agent consists of two components which cause foaming when brought together, these components are therefore contained in separate pre-mixes.

The foaming agent can, however, also be added only to the mixture of all the other components.

In addition, the starting materials used according to the invention can contain preservatives, such as benzoic acid, and thixotropic auxiliary agents, fillers or pigments.

The production of the moldings can take place by foaming and introduction of the cement in shapes with the smallest possible surface/volume ratio. During the setting, an increase in volume due to the foaming can be observed. While the cement is in a plastic phase, the compact surface can be peeled off. The porous moldings therefore have pores open to the outside. Complete setting can be carried out by leaving them to stand at 36° C./100% relative atmospheric humidity. The set cement can be ground to the appropriate particle fraction and screened to produce the granular material.

For filling bone defects, suitable granules according to the present invention are granules which have, for example, a particle size of 0.2–5 mm, particularly preferred particle size fractions being from 0.2 to 0.5 mm, from 0.5 to 1 mm, from 1 to 2 mm, from 2 to 3 mm, from 3 to 4 mm and from 4 to 5 mm.

Since it is known [J. F. Osborne, Zahnärztliche Mitteilungen 77, 840 (1987)] that the establishment of bone is prevented by sharp edges and that at the same time, the latter also increase the risk of inflammation, the granular material is preferably rounded off after the fractionation. Rounding off is carried out, for example, by rolling for 24 to 48 hours in $H_2O$ (distilled) or in dilute magnesium chloride solution. After rounding off, the granular material can then be filtered out on a screen corresponding to the particle size and washed free of splinters and fine particles.

The moldings obtained, e.g., granules, can then be autoclaved, e.g., by heating for 20 minutes to 121° C.

For interlocking in spinal-column surgery or in bone surgery (traumatology) and for bridging long bone defects, moldings in the form of parallelepipeds of different side-lengths can be used. Anatomically shaped porous bodies are particularly suitable for plastic surgery, e.g., as cheek-bone replacement or for chin reconstruction.

The porosity of the moldings can be expressed by the total pore volume in a manner known per se. The total pore volume can be determined, e.g., based on the differences in density of foamed and non-foamed material. For example, the total pore volume ($V_p$) (expressed as % by volume) can be obtained using Formula I:

$$V_p = \frac{100 \times (\rho k - g)}{\rho^k} \quad \text{Formula I}$$

$\rho k$ is the density of the compact material,
$\rho g$ is the density of the foamed material.

Another method for determining the total pore volume is mercury porosimetry. In this, mercury is pressed into the pores with increasing pressure. The pressure correlates with the pore size, the mercury volume pressed in at a certain pressure corresponding to the total volume of the pores of this size. The total pore volume ($V_p$) thus results from Formula II:

$$V_p = \frac{V_{Hg}}{V_g} \times 100\% \quad \text{Formula II}$$

In particular, the porosity of porous granular materials can be determined using the method of mercury porosimetry.

As component (a), the calcium aluminum fluorosilicate glasses disclosed in German Offenlegungsschrift 20 61 513 and European Patent Publication 0 023 013, and the strontium aluminum fluorosilicate glasses disclosed in the European Patent Publication 0 241 277 can be used. The aluminum fluorosilicate glass powders used according to the invention preferably comprise, in addition to oxygen:

| Component | Calculated as | wt. % |
|---|---|---|
| Si | $SiO_2$ | 20–60 |
| Al | $Al_2O_3$ | 10–50 |
| Ca | CaO | 0–40 |
| Sr | SrO | 0–40 |
| F | F | 1–40 |
| Na | $Na_2O$ | 0–10 |
| P | $P_2O_5$ | 0–10 | so that at least 1% by weight of CaO and/or SrO must be contained, and in total 0 to 20% by weight, calculated as oxides, of B, Bi, Zn, Mg, Sn, Ti, Zr, La or other trivalent lanthanoids, K, W, Ge and also further additives, which do not impair the properties and are physiologically acceptable. The glasses can be made X-ray visible by the addition of 10 to 20% by weight of $La_2O_3$.

The powder particles advantageously consist of:

| | | |
|---|---|---|
| Si as $SiO_2$ | 25–50% | by weight |
| Al as $Al_2O_3$ | 10–40% | by weight |
| Ca as CaO | 0–35% | by weight |
| Sr as SrO | 0–35% | by weight |
| F | 5–30% | by weight |
| Na as $Na_2O$ | 0–8% | by weight |
| P as $P_2O_5$ | 1–10% | by weight | so that at least 10% by weight of Ca (calculated as CaO) and/or Sr (calculated as SrO) must be contained, and 0–10% by weight of $B_2O_3$, $Bi_2O_3$, ZnO, MgO, $SnO_2$, $TiO_2$, $ZrO_2$, $La_2O_3$ or other oxides of trivalent lanthanoids, $K_2O$, $WO_3$, $GeO_2$ and also further additives, which do not impair the properties and are physiologically acceptable.

Powders which are particularly preferred contain:

| | | |
|---|---|---|
| Si as $SiO_2$ | 25–45% | by weight |
| Al as $Al_2O_3$ | 20–40% | by weight |
| Ca as CaO | 10–30% | by weight |
| F | 10–30% | by weight |
| Na as $Na_2O$ | 1–8% | by weight |
| P as $P_2O_5$ | 1–10% | by weight |

The glass powders used according to the invention have an average particle size (weight average) of at least 1 μm and preferably at least 3 μm. The average particle size (weight average) is 1–20 μm, preferably 3–15 μm and particularly preferably 3–10 μm. The particles have a maximum particle size of 150 μm, preferably 100 μm, particularly 60 μm.

The powders thus obtained are then optionally subjected to surface-treatment as described in European Patent Specification 0 023 013. For this purpose, the glass powders are surface-treated with acid, preferably at ambient temperature. For this purpose, substances containing acid groups are used, e.g., hydrochloric acid, sulfuric acid, nitric acid, acetic acid, propionic acid or perchloric acid, which form soluble calcium salts or strontium salts. The acids are used in a concentration of 0.01 to 10% by weight, preferably of 0.05 to 3% by weight. After the appropriate reaction time, the powders are separated from the solution and washed thoroughly, so that there are practically no soluble calcium or strontium salts left on the surface of the powder particles.

The polycarboxylic acids to be used as component (b) can also be the polycarboxylic acids known in the production of glass ionomer cement powders, e.g., polymaleic acid, polyacrylic acid, polyitaconic acid and mixtures thereof or copolymers, particularly the maleic acid acrylic acid copolymers and/or acrylic acid/itaconic acid copolymers known from the European Patent Specification 0 024 056. The average molecular weight of the polycarboxylic acids to be used according to the invention is more than 500. An average molecular weight of 1,000 to 20,000 is advantageous, and a particularly preferred average molecular weight is 3,000 to 10,000. The polycarboxylic acid is preferably used in concentrations of 5 to 50% by weight, based on component (a).

As component (d), a chelating agent, such as is described in German Offenlegungsschrift 23 19 715, can be contained. Tartaric acid is preferably used as the chelating agent.

With the open-pored moldings according to the present invention, bone substitute parts with satisfactory compatibility are obtained, through which, due to their open porosity, osseous material can grow well.

EXAMPLES

In all the Examples, a calcium aluminum fluorosilicate glass powder with the oxide composition shown in Table 1 is used.

TABLE 1

| | wt. % |
|---|---|
| Si as $SiO_2$ | 33.8 |
| Al as $Al_2O_3$ | 28.3 |
| Ca as CaO | 14.4 |
| Na as $Na_2O$ | 2.6 |
| P as $P_2O_5$ | 6.7 |
| F | 17.3 |

The average particle size is 5 μm.

EXAMPLE 1

100 parts by weight of the glass powder are mixed into a homogeneous powder with 0.5 parts by weight of sodium hydroboride (Merck Co.). 2 parts by weight of this powder are mixed into a homogeneous paste with a solution consisting of 35% of a copolymer of acrylic acid and maleic acid. (1:1, average molecular weight 7000), and 65% dist. $H_2O$. The material has a working time of approximately 4 minutes 30 seconds (calculated from the beginning of mixing) and is completely hard after 12–13 minutes. The material foams into a porous molding with pore sizes between 0.1 and 3mm. The properties of the porous material are shown in Table 2.

EXAMPLE 2

100 parts by weight of the calcium aluminum fluorosilicate glass powder are mixed into a homogeneous powder with 18 parts by weight of iron (II) sulphate (Merck Co.) and 20.4 parts by weight of the copolymer from Example 1. (The dry copolymer is stabilized with 0.9% by weight of benzoic acid, based on the copolymer).

3.4 parts by weight of the thus obtained powder mixture are mixed homogeneously for half a minute with 1 part by weight of a 30% $H_2O_2$ solution (Merck Co.). During the working time of approximately 5 minutes (calculated from the beginning of mixing), the material foams up and after approximately 15 minutes becomes a solid, foamed molding, with pore sizes between 0.1 and 1 mm. The properties of the porous material are shown in Table 2.

EXAMPLE 3

100 parts by weight of the calcium aluminum fluorosilicate glass powder are mixed into a homogeneous powder with 3.8 parts by weight of copper sulphate (Merck Co.), 1.9 parts by weight of aluminum powder (Merck Co.) and also 20.3 parts by weight of the copolymer from Example 1. (The dry copolymer is stabilized with 0.9% by weight of benzoic acid, based on the copolymer).

3.4 parts by weight of the thus obtained powder mixture are mixed homogeneously for half a minute with one part by weight of a 30% $H_2O_2$ solution (Merck Co.). During the working time of approximately 5 minutes (calculated from the beginning of mixing), the material foams up and after approximately 15 minutes becomes a solid, foamed molding.

EXAMPLE 4

A granular material of the particle size of 0.5-1 mm is produced from the porous materials of Examples 1-3 by crushing a subsequent screening. The bulk density and the specific surface of these granules are determined (according to Brunauer, Emmett and Teller, in which nitrogen is adsorbed and the observed volume change is measured—BET). The results are collected in Table 2.

EXAMPLE 5

Moldings were produced as described in Example 1, but without a foaming agent ($NaBH_4$). The values can be seen in Table 2.

TABLE 2

| Example | Foaming agent | Density of the mouldings [g/cm³] | Total pore vol. [%] | Interconnecting pore system | Granules 0.5-1 mm (Example 5) | |
|---|---|---|---|---|---|---|
| | | | | | Bulk density [g/cm³] | Specific surface [m²/g] |
| 1 | $NaBH_4$ | 0.7 | 65 | yes | 0.756 | 78 |
| 2 | $FeSO_4/H_2O_2$ | 1.34 | 33 | yes | 0.688 | 88 |
| 3 | $CuSO_4/Al/H_2O_2$ | 1.05 | 47.5 | yes | 0.551 | 37 |
| 5 (comparison) | — | 2.0 | 0 | no | | |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An open-pored molding containing the product of the foaming and setting of
   (a) an aluminum fluorosilicate glass,
   (b) at least one polycarboxylic acid with an average molecular weight of >500,
   (c) a foaming agent, other than carbonates and/or hydrogencarbonates,
   (d) optionally a chelating agent and
   (e) water,
   in which the total pore volume ($V_p$) of the molding is 30 to 70% by volume.

2. A molding according to claim 1 wherein the form is selected from the group consisting of granules parallelepipeds or anatomically shaped body as bone substitute material.

3. A molding according to claim 1, characterized in that the total pore volume ($V_p$) is 40 to 60% by volume 4. A molding according to claim 1, wherein (b) comprises one or more members of the group consisting of polymaleic acid, polyacrylic acid, polymaleic acid, polyacrylic acid, polyitaconic acid, maleic acid/acrylic acid copolymer and acrylic acid/itaconic acid copolymer.

5. A molding according to claim 1, wherein the foaming agent (c) is a metallic hydride, an aqueous solution of a gas which is expelled by acid, or a peroxide.

6. A molding according to claim 1, wherein the aluminum fluorosilicate glass comprises at least 1% by weight of CaO and/or SrO.

7. A molding according to claim 6, wherein the aluminum fluorosilicate comprises at least 10% by weight of CaO and/or SrO.

8. A process for the production of open-pored moldings, wherein
   (a) an aluminum fluorosilicate glass,
   (b) at least one polycarboxylic acid With an average molecular weight of >500,
   (c) a foaming agent, other than carbonates and/or hydrogencarbonates,
   (d) optionally a chelating agent and
   (e) water
   are homogeneously mixed together and foamed With simultaneous and/or subsequent forming and then set.

9. A process according to claim 8, wherein the moldings are formed to granules, parallelepipeds or anatomically shaped body as bone substitute material.

10. An implantable material which comprises a molding according to claim 1.

11. An implantable material according to claim 10, in the form of an anatomically shaped body.

* * * * *